(12) United States Patent
Kraus et al.

(10) Patent No.: US 8,138,358 B2
(45) Date of Patent: Mar. 20, 2012

(54) SYNTHESIS OF POLYCYCLIC PROCYANIDINS

(75) Inventors: George A. Kraus, Ames, IA (US); Yi Yuan, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 209 days.

(21) Appl. No.: 12/563,909

(22) Filed: Sep. 21, 2009

(65) Prior Publication Data

US 2010/0010240 A1 Jan. 14, 2010

Related U.S. Application Data

(63) Continuation of application No. 11/275,756, filed on Jan. 26, 2006, now Pat. No. 7,615,649.

(51) Int. Cl.
*C07D 493/18* (2006.01)
(52) U.S. Cl. ...................................................... 549/382
(58) Field of Classification Search .................... 549/382
See application file for complete search history.

(56) References Cited

U.S. PATENT DOCUMENTS

| | | | |
|---|---|---|---|
| 4,938,949 | A | 7/1990 | Borch et al. |
| RE34,878 | E | 3/1995 | Toyoshima et al. |
| 5,531,991 | A | 7/1996 | Cheng et al. |
| 6,126,940 | A | 10/2000 | Takahashi et al. |
| 6,200,569 | B1 | 3/2001 | Cheng |
| 6,312,753 | B1 | 11/2001 | Kealey et al. |
| 7,615,649 | B2 | 11/2009 | Kraus et al. |
| 2007/0173543 | A1 | 7/2007 | Kraus et al. |

FOREIGN PATENT DOCUMENTS

| | | |
|---|---|---|
| AU | 1380699 | 5/1999 |
| JP | 1040431 | 2/1989 |
| JP | 4210644 | 7/1992 |
| WO | WO-2005072726 A1 | 8/2005 |
| WO | WO-2007086847 A1 | 8/2007 |

OTHER PUBLICATIONS

"U.S. Appl. No. 11/275,756 Supplemental Notice of Allowability Sep. 30, 2009", 3 pgs.
"U.S. Appl. No. 11/275,756 Non-Final Office Action mailed Dec. 5, 2008", 10 pgs.
"U.S. Appl. No. 11/275,756, Notice of Allowance mailed Jun. 30, 2009", 6 pgs.
"U.S. Appl. No. 11/275,756, Response filed May 5, 2009 to Non Final Office Action mailed Dec. 5, 2008", 15 pgs.
"ARS Project: Naturally Occurring Insulin Enhancing Factors", (Project Number: 1235-51520-037-03), http://web.archive.org/web/20040405035230/http://www.ars.usda.gov/research/projects/projects.htm?ACCN_NO=407920, (archived Apr. 5, 2004), 1 pg.
"International Search Report for corresponding PCT Application No. PCT/US2006/002754", (Jul. 27, 2006), 4 pgs.
"Protein Facility Helps Diabetes Researcher", *The Innovator*, Iowa State University, Biotechnoloyg Instrumentation Facilities, (Jun. 28, 1996), 1 pg.

Anderson, R. A., et al., "An Improved Assay for Biologically Active Chromium", *Journal of Agriculture and Food Chemistry*, 26(5), (1970), 1219-1221.
Anderson, R. A., et al., "Isolation and Characterization of Polyphenol Type-A Polymers From Cinnamon With Insulin-Like Biological Activity", *Journal of Agricultural and Food Chemistry*, 52, (2004), 65-70.
Anderson, R., "Polyphenols From Cinnamon Increase Insulin Sensitivity: Functional and Clinical Aspects", *4th International Congress Dietary Antioxidants and Trace Elements, Vitamins and Polyphenols*, 4, (Abstract Only), http://www.ars.usda.gov/research/publications.htm?SEQ_NO_115=176887, (Apr. 2005), 2 pgs.
Beecher, G. R., "Proanthocyanidins: Biological Activities Associated with Human Health", *Pharmaceutical Biology*, 42, Supplement, 2004, 2-20.
Berrio, L. F., et al., "Insulin Activity: Stimulatory Effects of Cinnamon and Brewer's Yeast as Influenced by Albumin", *Hormone Research*, 37(6), (1992), 225-229.
Broadhurst, C. L., et al., "Insulin-Like Biological Activity of Culinary and Medicinal Plant Aqueous Extracts in Vitro", *J. Agric. Food Chem*, 48, (2000), 849-852.
Carter, J. S., et al., "Non-Insulin-Dependent Diabetes Mellitus in Minorities in the United States", *Annals of Internal Medicine*, 125(3), (Aug. 1, 1996), 221-232.
Foreman, J., "Cinnamon Joins Chlolesterol Battle", www.myhealthsense.com, http://web.archive.org/web/20041025074606/http://www.myhealthsense.com/F040824_cinnamon.html, (2004), 3 pgs.
Gray, A. M., et al., "Pancreatic and Extra-Pancreatic Effects of the Traditional Anti-Diabetic Plant, *Medicago sativa* (lucerne)", *British Journal of Nutrition*, 78(2), (Aug. 1997), 325-334.
Hashimoto, F., et al., "Tannins and Related Compounds XC1 8-C-Ascorbyl(—)-Epigallocatechin 3-O-Gallate and Novel Dimeric Flavan-3-ols, Oolonghomobisflavans A and B, from Oolong Tea(3).", *Chem. Pharm. Bull*, 37(12), (1989), 3255-3263.
Impari-Radosevich, J., et al., "Regulation of PTP-1 and Insulin Receptor Kinase by Fractions From Cinnamon: Implications of Cinnamon Regulation of Insulin Signalling", *Hormone Research*, 50, 1998, 177-182.
Jarvill-Taylor, K., et al., "A Hydroxychalcone Derived From Cinnamon Functions as a Mimetic for Insulin in 3T3-L1 Adlpocytes", *Journal of the American College of Nutrition*, 20(4), (2001), 327-336.
Jurd, et al., "", *Tetrahedron* vol. 21, (Jan. 9, 1965), 1471-1483.
Jurd, L., et al., "Anthocyanidins and Related Compounds—VII Reactions of Flavylium Salts with 5,5-Dimethyl-1,3-Cyclohexanedione at pH 5.8", *Tetrahedron*, 21, 1965, 3697-3705.
Khan, A., et al., "Cinnamon Improves Glucose and Lipids of People With Type 2 Diabetes", *Diabetes Care*, 26(12), (2003), 3215-3218.
Khan, A., et al., "Insulating Potentiating Factor and Chromium Content of Selected Foods and Spices", *Biological Trace Element Research*, 24, (1990), 183-188.
Kondo, K., et al., "Conversion of procyanidin B-type (catechin dimmer) to A-type: evidence for abstraction of C-2 hydrogen in catechin during radical oxidation", *Tetrahedron Letters*, 41(4), (2000), 485-488.

(Continued)

Primary Examiner — Bernard Dentz
(74) *Attorney, Agent, or Firm* — Schwegman, Lundberg & Woessner, P.A.

(57) ABSTRACT

The invention provides compounds that are A-type procyanidins. The compounds can be prepared by reacting flavylium salts with catechins or analogs thereof, for example, under anhydrous conditions in alcohol.

9 Claims, 5 Drawing Sheets

OTHER PUBLICATIONS

Mackenzie, D., "Cinnamon Spice Produces Healthier Blood", NewScientist.com, http://www.newscientist.com/article.ns?id=dn4413&print=true, (Nov. 2003), 2 pgs.

McBride, J., "Cinnamon Extracts Boost Insulin Sensitivity", *Agricultural Research*, (Jul. 2000), p. 21.

Morimoto, S., et al., "Tannins and Related Compounds. LIX. Aesculitannins, Novel Proanthocyanidins with Doubly-bonded Structures from *Aesculus hippocastanum* L.", *Chemical & Pharmaceutical Bulletin*, 35(12), (1987), 4717-4729.

Nonaka, G.-I., et al., "Tannins and Related Compounds. Part 13. Isolation and Structures of Trimeric, Tetrameric, and Pentameric Proanthicyanidins From Cinnamon", *Journal of Chemical Society, Perkin Transactions I*, (1993), 2139-2145.

Nonaka, Gen-Ichiro, "Tannins and Related Compounds. L1. Structures of Proanthocyanidin A-1 and Related Compounds", *Chem. Pharm. Bull*, 35(1), (1987), 149-155.

Pomilio, A., et al., "Uber die Konstitution der Kondensationsprodukte von Phenolen mit Flavyliumsalzen (On the Constitution of Condensation Products of Phenols with Flavylium Salts)", *Justus Liebigs Annalen der Chemie> Heft 4*, (1977), 597-601.

Reitman, V., "For Type 2 Diabetes, Dash of Cinnamon May Help", *The Daily Camera*, http://www.holistic.com/holistic/learning.nsf/31efaf81faf8de6a87256906004b973a/5f12cc099fc17b2887256e2b007eb98e!OpenDocument, (Jan. 26, 2004), 3 pgs.

Schoene, N. W., et al., "Water-Soluble Polymeric Polyphenols From Cinnamon Inhibit Proliferation and Alter Cell Cycle Distribution Patterns of Hematologic Tumor Cell Lines", *Cancer Letters*, 230(1), (Dec. 8, 2005), 134-140.

Soltis, L., et al., "Effects of Dietary Cinnamon on Insulin-Mediated Physiological Parameters", *The FASEB Journal*, 13(5), (Abstract No. 669.1), Experimental Biology 99(r)—Abstracts (Part II), (1989), p. A884.

A-1A  A-1B  A-1C

A-1D  A-1E  A-1F

A-1G  A-1H  A-1I

D-1A

D-1B

D-1C

D-1D

D-1E

SYNTHESIS OF POLYCYCLIC PROCYANIDINS

RELATED APPLICATION

This application is a continuation under 37 C.F.R. 1.53 (b) of U.S. patent application Ser. No. 11/275,756, filed Jan. 26, 2006 now U.S. Pat. No. 7,615,649, the content of which is incorporated herein by reference in its entirety.

STATEMENT OF GOVERNMENT RIGHTS

The invention was made with a grant from the Government of the United States of America (USDA/ARS Grant No. 58-3K95-5-1073). The Government has certain rights to the invention.

BACKGROUND OF THE INVENTION

Despite extensive diabetes research, the prevention and control of type 2 diabetes mellitus (type 2 DM) remain unclear. Diet has been shown to play a definite role in the onset of type 2 DM, and the diets commonly consumed in the United States and other westernized countries appear to increase the incidence of diabetes (J. S. Carter et al., *Ann. Int. Med.*, 125, 221 (1996)). The high refined sugar and high fat content of U.S. diets are likely to be partly responsible, but the low intake of traditional herbs, spices, and other plant products may also be involved. The recommended use of plants in the treatment of diabetes dates back to approximately 1550 BCE (A. M. Gray et al., *Br. J. Nutr.*, 78, 325 (1997)). For the majority of the world population, drug treatment for diabetes is not feasible and alternative treatments need to be evaluated.

Plants are important not only for the control of type 2 DM but also for its prevention, especially for people with elevated levels of blood glucose and glucose intolerance who have a greater risk of developing diabetes. Common spices such as cinnamon, cloves, and bay leaves display insulin potentiating activity in vitro (A. Khan et al., *Biol. Trace Elem. Res.*, 24, 183 (1990)). It was thought that these spices might also have high chromium (Cr) concentrations, because biologically active forms of Cr potentiate insulin activity. However, there are no correlations between total Cr concentrations and insulin potentiating activity in these plant products (See, A. Khan et al., cited above). Only a small portion of the total Cr in biological systems is associated with insulin potentiating activity.

From an aqueous extract of commercial cinnamon, R. A. Anderson et al., *J. Agric. Food Chem.*, 52, 65 (2004) have identified polyphenolic polymers that increase glucose metabolism roughly 20-fold in vitro in the epididymal fat cell assay. These appear to be rather unique, because other cinnamon or similar compounds display little or no biological activity. Additionally, approximately 50 plant extracts have also been investigated in this assay, and none have shown activity equal to that of cinnamon (C. L. Broadhurst et al., *J. Agric. Food Chem.*, 48, 849 (2000)).

Recently, R. A. Anderson et al., (cited above) extracted cinnamon samples with acetic acid and ethanol and isolated fractions with insulin-enhancing activity using HPLC. Spectral analysis indicated the presence of, inter alia, doubly-linked aromatic polyphenols. The structures are shown below (Formula I).

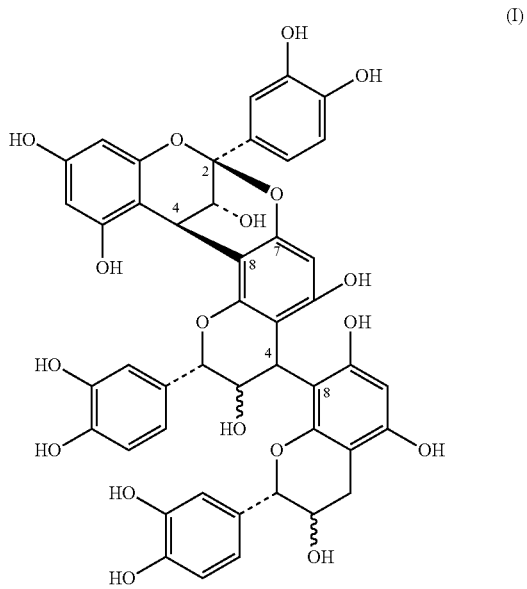

The fractions containing these polyphenols, or A-type proanthocyanidins, were shown to have insulin-enhancing biological activity in an in vitro assay measuring the insulin-dependent effects on glucose metabolism. See, R. A. Anderson et al., *J. Agric. Food Chem.*, 26, 1219 (1978). The fractions also were active as antioxidants. N. W. Schoene et al., *Nutr. Res.*, 20, 47 (2000). These same compounds have been shown to inhibit phosphotyrosine phosphatases in the insulin-receptor domain and to activate insulin receptor kinase, and to function as a mimetic for insulin in 3T3-L1 adipocytes. J. Imparl-Radosevich et al., *Hormone Res.*, 50, 177 (1998); *J. Am. Coll. Nutr.*, 20, 327 (2001). Water-soluble polymeric polyphenols from cinnamon have also been shown to inhibit proliferation and to alter cell cycle distribution patterns of hematologic tumor cell lines. N. W. Schoene et al., *Cancer Lett.*, 230, 134 (2005).

However, compounds of Formula I are difficult to synthesize, as are intermediates useful in such syntheses. S. Morimoto et al., *Chem. Pharm. Bull.*, 35, 4717 (1987) prepared proanthocyanins A-G (III) and A-7 (IV) in low yield by the oxidation of procyanidin B-5 (II) with hydrogen peroxide in the presence of sodium bicarbonate. See FIG. 1. A. Pomilo et al., *Liebigs. Ann. Chem.*, 597 (1977) reacted flavylium perchloride (V) with (+) catechin in aqueous methanol to yield compound VII in 2-3% yield. (See FIG. 2). Therefore, there is a continuing need for methods to prepare bioactive polyphenols, such as those derived from cinnamon.

SUMMARY OF THE INVENTION

The present invention provides a one-step synthesis of A-type procyanidins form benzopyrylium salts and phenols, such as flavins. For example, the present invention provides a method for the preparation of a compound of Formula A:

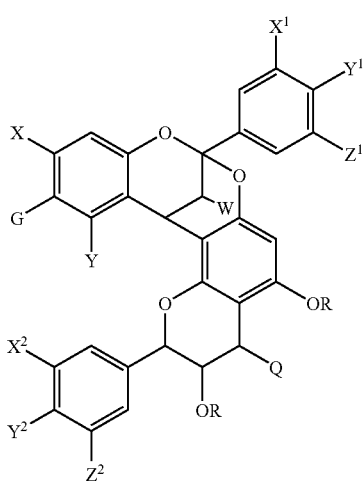

(A)

wherein X, Y, $X^1$, $Y^1$, $Z^1$, $X^2$, $Y^2$, and $Z^2$ are individually H, OH, $N(R)_2$, $(C_1$-$C_6)$alkoxy, or $(C_2$-$C_6)$alkanoyloxy; G is H, OH, $(C_1$-$C_6)$alkoxy, $(C_2$-$C_6)$alkanoyloxy, $N(R)_2$ or $NO_2$; W is H, OH, $(C_2$-$C_6)$alkyl; $(C_1$-$C_6)$alkoxy, $(C_1$-$C_6)$hydroxyalkyl or $(C_1$-$C_6)$alkoxycarbonyl$(C_1$-$C_6)$alkyl; Q is H or a single bond to $C_8$ of a compound of formula C wherein Q is H; each R is individually H, $(C_1$-$C_4)$alkyl, $(C_2$-$C_6)$alkanoyl or $(C_6$-$C_{14})$arylC(O) wherein aryl, such as phenyl, can be substituted with 1, 2 or 3 X; by reacting a compound of Formula B:

(B)

wherein $An^-$ is a pharmaceutically acceptable anion, with a compound of Formula (C):

(C)

in solution in an anhydrous $(C_1$-$C_4)$alkanol or mixture thereof, under ambient conditions, e.g., at about 20°-50° C. for about 1-24 hours and; isolating the compound of Formula A.

The present invention also provides a method to prepare a compound of Formula D:

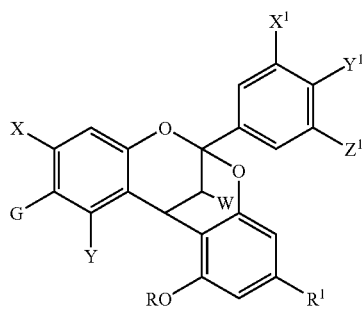

(D)

wherein X, Y, Z, W, G and R are as defined above by reacting a compound of Formula (B) with a compound of Formula (E):

(E)

wherein $R^1$ is OH or hydroxy$(C_1$-$C_6)$alkyl in solution in an anhydrous $(C_1$-$C_4)$alkanol or mixture thereof, under ambient conditions, e.g., at about 20-50° C. for about 1-24 hours and; isolating the compound of Formula D.

In both cases, the starting materials are dissolved at moderate concentrations (0.02-0.2M) in an about 1:1 molar ratio, in methanol. Added water or aqueous buffer is not required. Yields are generally ≧70% after purification by simple chromatographic techniques, such as flash chromatography.

Novel compounds of Formula A or D are also within the scope of the invention. The compounds are useful as intermediates to prepare complex proanthocyanidins, such as compounds shown in R. A. Anderson et al. (2004), cited above or 8, 9, 12, 13, 21, 20 and 14, as depicted in S. Morimoto et al., *Chem. Pharm. Bull.*, 35, 4717 (1987). Certain of these compounds are useful as intermediates to make other compounds of Formulas A or D, e.g., hydroxy groups can be converted into methoxy groups by reaction with $CH_2N_2$ or dimethyl sulfate, or esterified with alkanoyl or aroyl chlorides. Nitro groups can be reduced to amino groups and acylated, alkylated or otherwise substituted.

The present methods are useful to make naturally-occurring polyphenols and non-naturally occurring polyphenols and non-naturally occurring analogs thereof that can have beneficial effects on glucose, insulin and blood lipids. Such compounds can be used to treat diabetes by enhancing the effect of both in vivo and exogenously-administered insulin. Thus, compounds of Formula A and D can improve insulin receptor function by activating insulin receptor kinase and inhibiting insulin receptor phosphatases, thus leading to increased insulin sensitivity, and improved utilization of glucose by mammals, such as human diabetics in need of such treatment. See, J. Impari-Radosevich et al., *Hormone Res.*, 50, 177 (1998); K. J. Jarvill-Taylor et al., *J. Am. Coll. Nutr.*, 20, 327 (2001) and A. Khan et al., *Diabetes Care,* 26, 3215 (2003). Compounds of Formula A and D can also alter proliferative signals that regulate progression through the cell cycles of certain tumor cell lines, and may be useful to treat cancer. See, N. W. Schoene et al., *Cancer Lett.,* 230, 134 (2000). Type A procyanidins have also been reported to exhibit antimicrobial, antiviral and antiprotozoal activity.

DETAILED DESCRIPTION OF THE INVENTION

Figure 1:
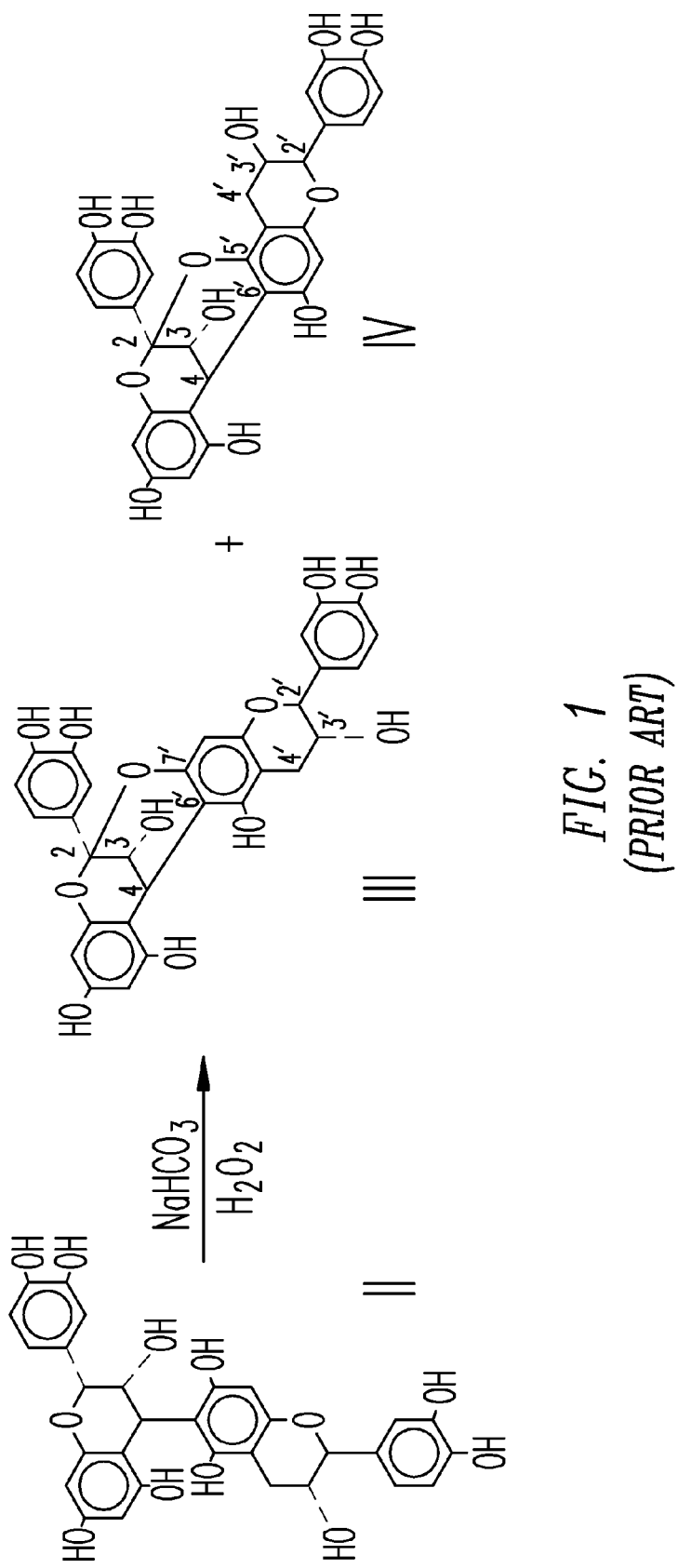
FIG. 1 depicts a prior art synthetic route to proanthocyanins.
Figure 2:
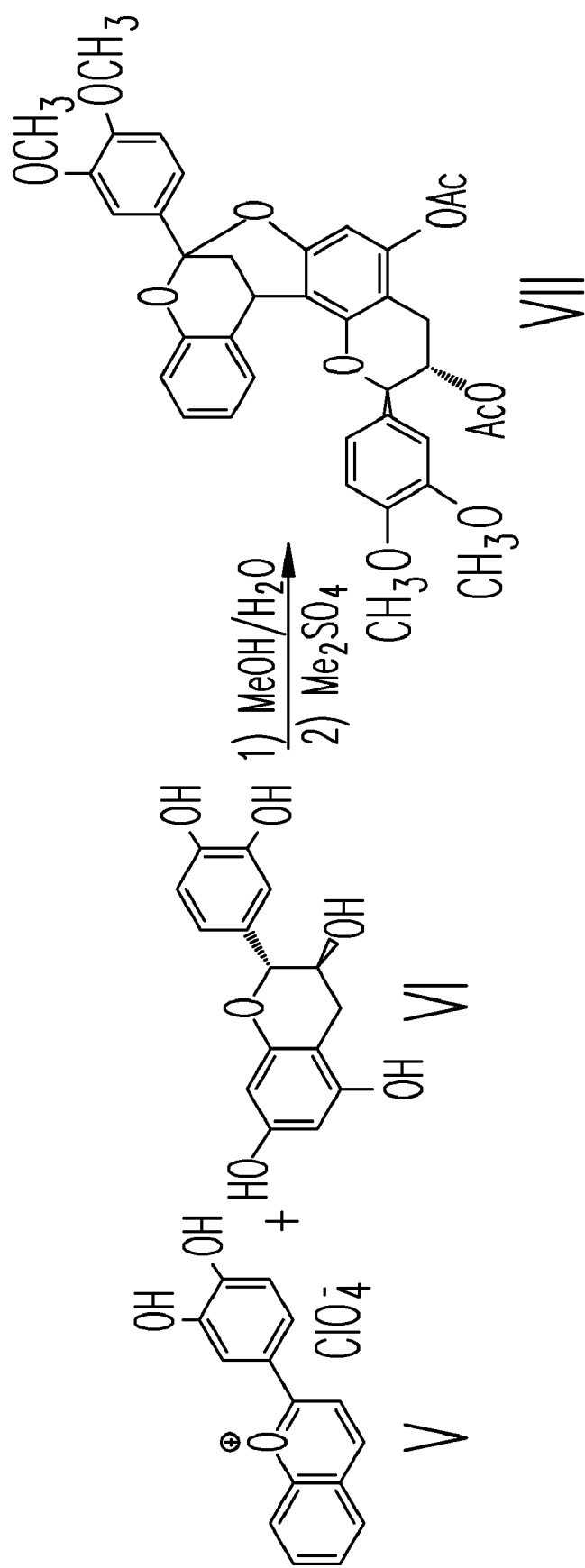
FIG. 2 depicts a prior art synthetic route to condense flavylium salts with phenols.
Figure 3:
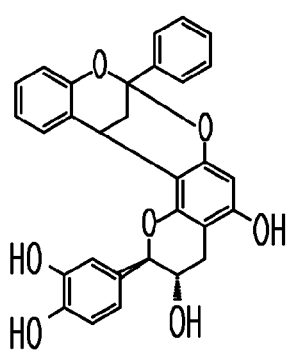
FIG. 3 depicts the structures of some of the compounds prepared by the present method.
Figure 3:
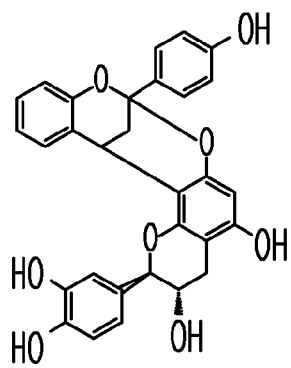
Figure 3:
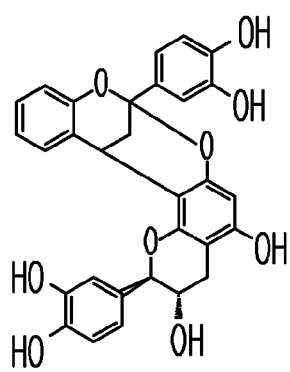
Figure 3:
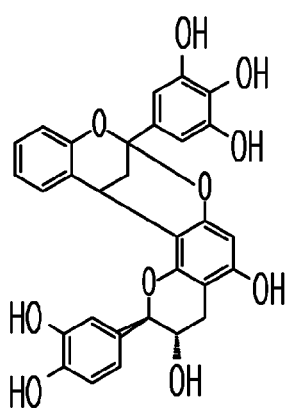
Figure 3:
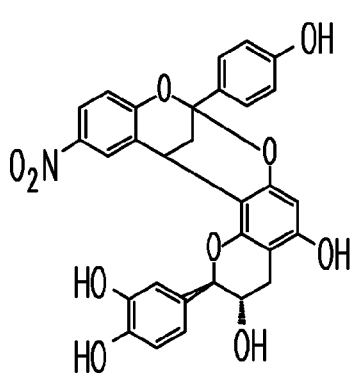
Figure 3:
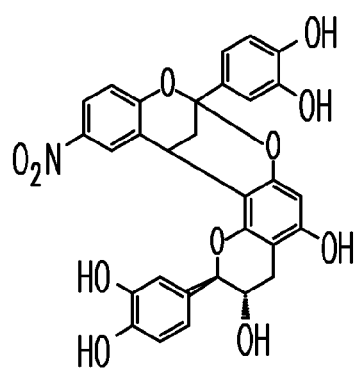
Figure 3:
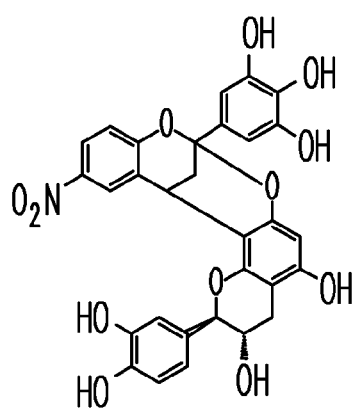
Figure 3:
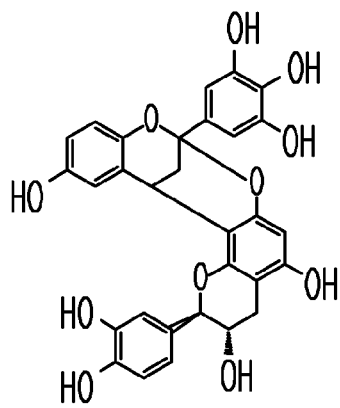
Figure 3:
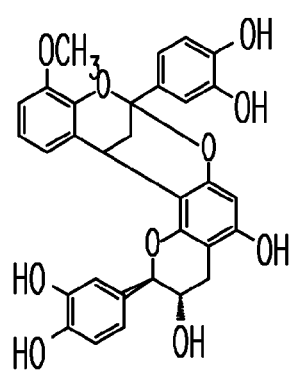
Figure 3:
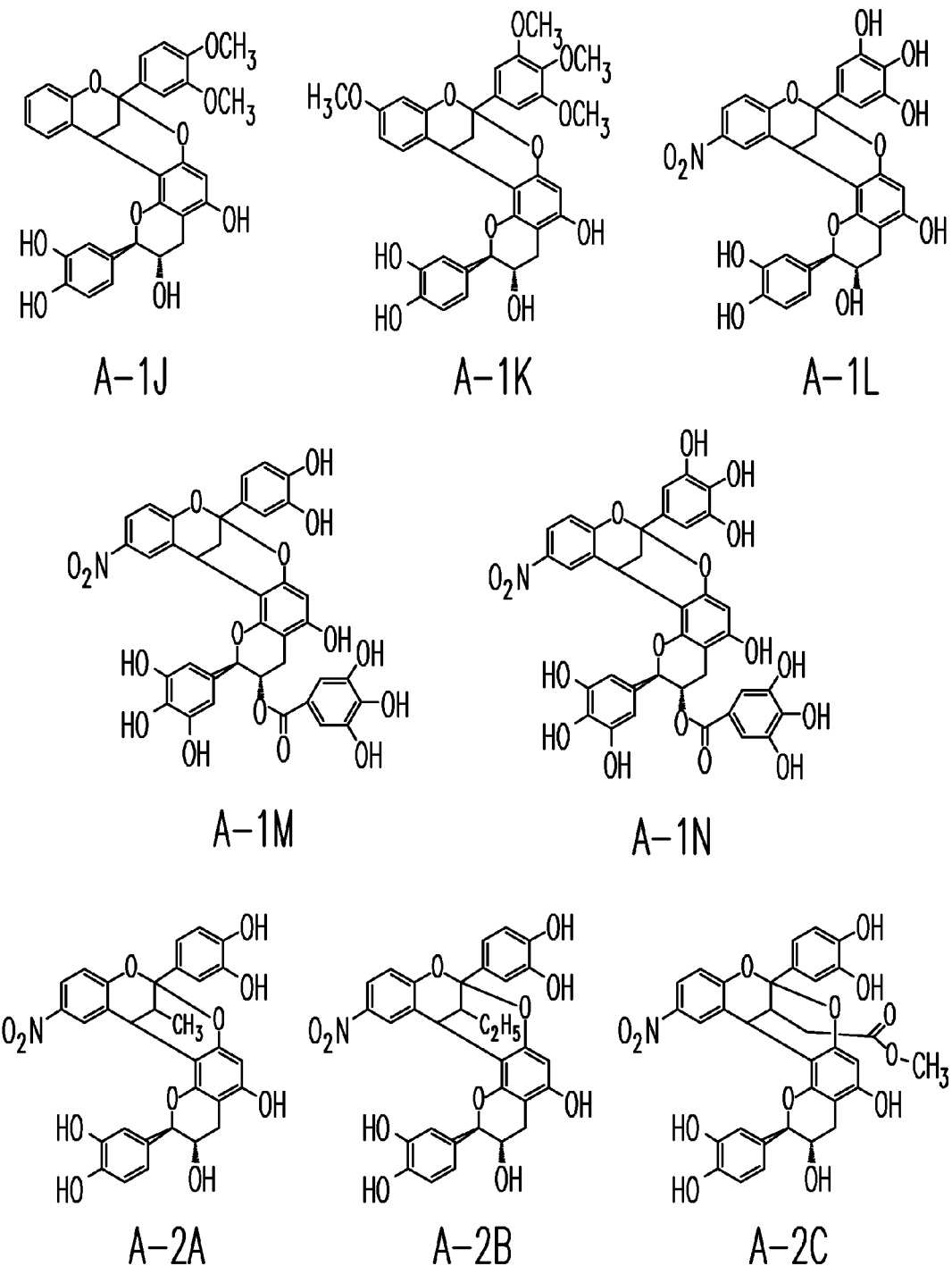
Figure 3:
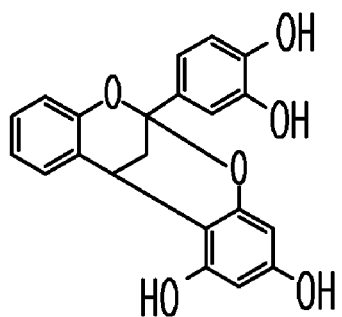
Figure 3:
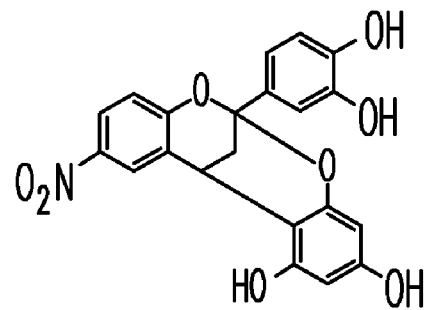
Figure 3:
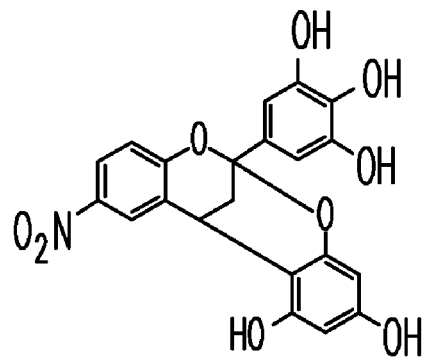
Figure 3:
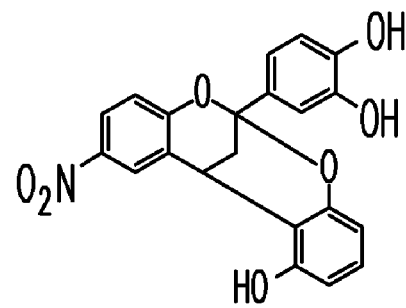
Figure 3:
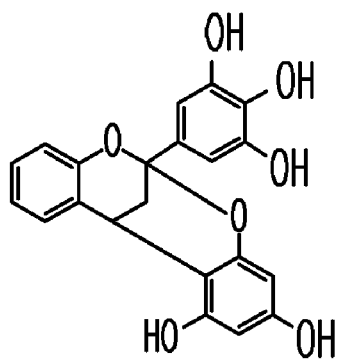

Alkyl, alkoxy, hydroxyalkyl, alkanoyloxy, etc. denote both straight and branched alkyl groups as well as cycloalkyl or (cycloalkyl)alkyl; but reference to an individual alkyl group such as Apropyl@ embraces only the straight chain group, a branched chain isomer such as Aisopropyl@ being specifically referred to. Aryl denotes a phenyl substituent or an ortho-fused bicyclic or tricyclic carbocyclic substituent having about nine to fourteen ring atoms in which at least one ring is aromatic.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-oxidant, anti-tumor or insulin-potentiating activity using the standard tests referenced herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, hexyl, cyclopropyl, cyclobutyl, cyclopentyl, cyclohexyl, cyclopropylmethyl, cyclobutylmethyl, cyclopentylmethyl, 2-cyclopropylethyl, 2-cyclobutylethyl, or $(C_1-C_6)$alkoxy can be methoxy, ethoxy, propoxy, isopropoxy, butoxy, iso-butoxy, sec-butoxy, pentoxy, 3-pentoxy, or hexyloxy; acetyl, propanoyl or butanoyl; hydroxy$(C_1-C_6)$alkyl can be alkyl substituted with 1 or 2 OH groups, such as alkyl substituted with 1 or 2 OH groups, such as hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 3,4-dihydroxybutyl, 1-hydroxypentyl, 5-hydroxypentyl, 1-hydroxyhexyl, or 6-hydroxyhexyl.

In compounds of Formulas A, B, C, D and E:
preferably, G is H, $NO_2$ or $(C_1-C_4)$alkoxy, e.g., methoxy;
preferably, $X^1$ is H, OH or $(C_1-C_4)$alkoxy, e.g., methoxy;
preferably, $Y^1$ is H, OH or $(C_1-C_4)$alkoxy, e.g., methoxy;
preferably, $Z^1$ is H, OH or $(C_1-C_4)$alkoxy, e.g., methoxy;
preferably, X and Y are H, OH, $NH_2$, or $(C_1-C_4)$alkoxy, e.g., methoxy;
preferably, $X^2$ and/or $Y^2$ are OH;
preferably, $Z^2$ is H or $(C_1-C_4)$alkoxy, e.g., methoxy;
preferably, W is H, OH, $(C_1-C_4)$alkyl, $(C_1-C_4)$alkoxy, or $(C_1-C_4)$alkoxycarbonyl$(C_1-C_2)$alkyl;
preferably, $N(R)_2$ is $NH_2$;
preferably, each R is H or substituted phenylC(O), e.g., 3,4,5-trihydroxybenzoyl; and
preferably, $R^1$ is OH.

Specific embodiments include the preparation of compounds of Formulas A or D wherein $X^1$ is H and $Y^1$ and $Z^1$ are OH or $OCH_3$; or wherein $X^1$, $Y^1$, and $Z^1$ are each OH or $OCH_3$; or wherein $X^1$ and $Y^1$ are H and $Z^1$ is OH.

Specific embodiments include the preparation of compounds of Formula A or D, wherein $X^2$ and $Y^2$ are OH and $Z^2$ is H; or wherein each of $X^2$, $Y^2$ and $Z^2$ is OH.

Specific embodiments include the preparation of compounds of Formulas A or D wherein W is H, OH or $(C_1-C_4)$ alkyl, e.g., methyl or ethyl, or is methoxycarbonylmethyl.

Specific embodiments include the preparation of compounds of Formulas A or D wherein R is H.

Specific embodiments include the preparation of compounds of Formulas A or D wherein G is H or $NO_2$.

Specific embodiments include the preparation of compounds of Formula D wherein $R^1$ is OH and/or R is H.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium), alkaline earth metal (for example calcium or magnesium) or zinc salts can also be made.

The compounds of Formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes, or by inhalation or insufflation.

Thus, the present compounds may be systemically administered, e.g., orally, in combination with a pharmaceutically acceptable vehicle such as an inert diluent or an assimilable edible carrier. In view of the fact that useful compounds of Formulas A and D are either natural products or analogs or prodrugs thereof, it is preferred to combine an effective dose of one or more of said compounds with a foodstuff, intended for oral ingestion. Such foods can include those which typically contain sugar, such as cereals, "energy bars," sports drinks, milk, flavored waters, shakes, breads, cookies, cakes, candy, and other confections.

They may also be enclosed in hard or soft shell gelatin capsules as powders, pellets or suspensions or may be compressed into tablets. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices, such as patches, infusion pumps or implantable depots.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Thus, for the treatment of diabetes, the present compounds can be provided as kits, e.g., as premeasured vials or preloaded syringes in combination with separately packaged insulin-delivery devices, along with instructions for use of the kit to treat diabetes.

The pharmaceutical dosage forms suitable for injection, infusion or inhalation can include sterile aqueous solutions or dispersions. Sterile powders can be prepared comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, cellulose ethers, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of Formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular compound or salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 mg to as much as 1-3 g, conveniently 10 to 1000 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline. For example, as much as about 0.5-3 g of a compound of Formula I can be dissolved in about 125-500 ml of an intravenous solution comprising, e.g., 0.9% NaCl, and about 5-10% glucose. Such solutions can be infused over an extended period of up to several hours, optionally in conjunction with other anti-viral agents, antibiotics, etc. The active ingredient can also be orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will be described further by reference to the following detailed Examples.

Example 1

Table 1 depicts the reaction of catechin hydrate (C-1) with various flavylium salts (B-1) to yield compounds of Formula A-1.

TABLE 1

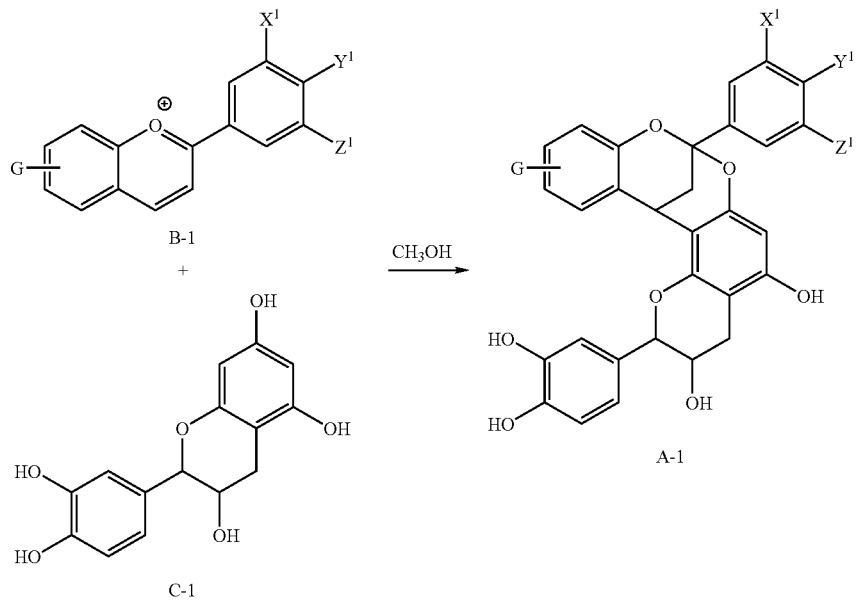

| Flavan | G | $X^1$ | $Y^1$ | $Z^1$ | Yield (%) | A-1 |
|---|---|---|---|---|---|---|
| (+)-catechin | H | H | H | H | 82 | A-1A |
| (+)-catechin | H | H | OH | H | 79 | A-1B |
| (+)-catechin | H | H | OH | OH | 89 | A-1C |
| (+)-catechin | H | OH | OH | OH | 80 | A-1D |
| (+)-catechin | 6-$NO_2$ | H | OH | H | 83 | A-1E |
| (+)-catechin | 6-$NO_2$ | H | OH | OH | 76 | A-1F |
| (+)-catechin | 6-$NO_2$ | OH | OH | OH | 81 | A-1G |
| (+)-catechin | 6-OH | OH | OH | OH | 47 | A-1H |
| (+)-catechin | 8-$OCH_3$ | H | OH | OH | 70 | A-1I |
| (+)-catechin | H | H | $OCH_3$ | $OCH_3$ | 83 | A-1J |
| (+)-catechin | 7-$OCH_3$ | $OCH_3$ | $OCH_3$ | $OCH_3$ | 33 | A-1K |
| (−)-epicatechin | 6-$NO_2$ | OH | OH | OH | 81 | A-1L |
| (−)-Epigallocatechin gallate | 6-$NO_2$ | H | OH | OH | 86 | A-1M |
| (−)-Epigallocatechin gallate | 6-$NO_2$ | OH | OH | OH | 71 | A-1N |

Example 2

Table 2 depicts the reaction of three 3-substituted flavins to yield compounds of Formula A-2.

TABLE 2

| $W^1$ | $W^2$ | Yield (%) | A-2 |
|---|---|---|---|
| $CH_3$ | $CH_3$ | 75 | A-2A |
| $C_2H_5$ | $C_2H_5$ | 79 | A-2B |
| $CH_2COOH$ | $CH_2COOCH_3$ | 83 | A-2C |

Example 3

Table 3 depicts the reaction of various flavylium perchloride salts with various phenols to yield compounds of Formula D-1. Generally, in all cases, the reactions proceeded to provide high (≧70%) yields of A-1, A-2 or D-1 under ambient temperatures and pressures.

TABLE 3

| $R^1$ | G | $X^1$ | $Y^1$ | $Z^1$ | Yield (%) | D-1 |
|---|---|---|---|---|---|---|
| OH | H | H | OH | OH | 76 | D-1A |
| OH | 6-$NO_2$ | H | OH | OH | 80 | D-1B |

TABLE 3-continued

| | | | | | | |
|---|---|---|---|---|---|---|
| OH | 6-NO$_2$ | OH | OH | OH | 82 | D-1C |
| H | 6-NO$_2$ | H | OH | OH | 71 | D-1D |
| OH | H | OH | OH | OH | 73 | D-1E |

A. General Procedure:

To a solution of catechin or other nucleophile in methanol (0.02-0.2 M) was added flavylium salt (1.0 to 1.2 equivalent) at room temperature. The mixture was stirred at room temperature to 50° C. for 1-24 hours (monitored by TLC and NMR). After the reaction finished, the mixture was concentrated and absorbed on a small amount of silica gel. The pure product was isolated by purification of the crude mixture using flash column chromatography on silica gel with a mixture of hexane, ethyl acetate and methanol as eluent.

B. A Typical Procedure for the Synthesis of Compound A-1A:

To a solution of (+)-catechin hydrate (C-1) (925 mg, 3.0 mmol) in methanol (65 mL) was added 2-Phenylbenzopyrylium perchlorate salt (B-1; G, X$^1$, Y$^1$, Z$^1$=H) (920 mg, 3.0 mmol) at room temperature (25° C.). The solution was stirred at r.t. for 15 hours. The solution was concentrated and absorbed on a small amount of silica gel. The crude product was purified on column chromatography on silica gel using hexane:ethyl acetate:methanol (2:1:0-1:1.5:0.005) as eluent. 1.23 g compound A-1A was collected in 82.2% yield. The product contains two stereoisomers in a ratio of 60:40 indicated by NMR spectra.

C. Spectral Data:

Compound A-1A:

(2R,3S,8S,14S)-2-(3,4-dihydroxyphenyl)-8-phenyl-3,4-dihydro-2H,14H-8,14-methanochromeno[7,8-d][1,3]benzodioxocine-3,5-diol and (2R,3S,8R,14R)-2-(3,4-dihydroxyphenyl)-8-phenyl-3,4-dihydro-2H,14H-8,14-methanochromeno[7,8-d][1,3]benzodioxocine-3,5-diol Yield=82%

Major isomer (60%)

$^1$H NMR (400 MHz, CD$_3$OD) δ 7.70-7.61 (m, 2H), 7.42-7.31 (m, 3H), 7.14 (dd, J=7.6, 1.6 Hz, 1H), 7.10-6.98 (m, 2H), 6.93-6.72 (m, 4H), 6.09 (s, 1H), 4.58 (d, J=8.0 Hz, 1H), 4.33 (t, J=3.0 Hz, 1H), 4.02 (m, 1H), 2.95 (dd, J=16.4, 5.6 Hz, 1H), 2.51 (dd, J=16.4, 8.0 Hz, 1H), 2.22 (dd, J=13.2, 3.0 Hz, 1H), 2.18 (dd, J=13.2, 3.0 Hz, 1H).

Minor isomer (40%)

$^1$H NMR (400 MHz, CD$_3$OD) δ 7.70-7.61 (m, 2H), 7.42-7.31 (m, 3H), 7.26 (dd, J=7.6, 1.6 Hz, 1H), 7.10-6.98 (m, 2H), 6.93-6.72 (m, 4H), 6.10 (s, 1H), 4.71 (d, J=8.0 Hz, 1H), 4.27 (t, J=3.0 Hz, 1H), 3.96 (m, 1H), 2.87 (dd, J=16.4, 5.6 Hz, 1H), 2.55 (dd, J=16.4, 8.0 Hz, 1H), 2.16 (dd, J=13.2, 3.0 Hz, 1H), 2.10 (dd, J=13.2, 3.0 Hz, 1H).

Major isomer (60%)

$^{13}$C NMR (1100 MHz, CD$_3$OD) δ 155.74, 153.69, 152.71, 151.99, 146.39, 146.33, 146.31, 143.34, 132.05, 129.59, 129.22, 129.13, 128.95, 128.58, 128.33, 126.74, 122.04, 120.24, 116.76, 116.26, 115.52, 106.92, 102.83, 99.92, 96.31, 82.97, 68.69, 34.53, 29.27, 28.00.

Minor isomer (40%)

$^{13}$C NMR (1100 MHz, CD$_3$OD) δ 155.78, 153.64, 152.48, 152.03, 146.39, 146.33, 146.31, 143.34, 132.21, 129.59, 129.22, 129.13, 128.95, 128.58, 128.39, 126.74, 122.04, 120.36, 116.76, 116.04, 115.52, 106.75, 102.48, 99.90, 96.22, 83.51, 68.76, 34.59, 28.63, 27.95.

HRMS (EI) m/z 496.1530 (M, 496.1522 calcd for C$_{30}$H$_{24}$O$_7$).

MS (EI) m/z 496 (11), 207 (100), 178 (39), 152 (58), 131 (70).

Compound A-1B:

(2R,3S,8S,14S)-2-(3,4-dihydroxyphenyl)-8-(4-hydroxyphenyl)-3,4-dihydro-2H,14H-8,14-methanochromeno[7,8-d][1,3]benzodioxocine-3,5-diol and (2R,3S,8R,14R)-2-(3,4-dihydroxyphenyl)-8-(4-hydroxyphenyl)-3,4-dihydro-2H,14H-8,14-methanochromeno[7,8-d][1,3]benzodioxocine-3,5-diol Yield=79%

Major isomer (55%)

$^1$H NMR (400 MHz, CD$_3$OD) δ 7.54-7.48 (m, 2H), 7.12 (d, J=7.2 Hz, 1H), 7.09-6.70 (m, 8H), 6.11 (s, 1H), 4.59 (d, J=8.4 Hz, 1H), 4.35 (t, J=3.0 Hz, 1H), 3.98 (m, 1H), 3.01 (dd, J=16.4, 5.6 Hz, 1H), 2.52 (dd, J=16.4, 8.4 Hz, 1H), 2.25 (dd, J=13.2, 3.0 Hz, 1H), 2.16 (dd, J=13.2, 3.0 Hz, 1H).

Minor isomer (45%)

$^1$H NMR (400 MHz, CD$_3$OD) δ 7.54-7.48 (m, 2H), 7.27 (d, J=7.2 Hz, 1H), 7.09-6.70 (m, 8H), 6.12 (s, 1H), 4.71 (d, J=8.4 Hz, 1H), 4.31 (t, J=3.0 Hz, 1H), 4.04 (m, 1H), 2.92 (dd, J=16.4, 5.6 Hz, 1H), 2.57 (dd, J=16.4, 8.4 Hz, 1H), 2.19 (dd, J=13.2, 3.0 Hz, 1H), 2.13 (dd, J=13.2, 3.0 Hz, 1H).

Compound A-1C:

(2R,3S,8S,14S)-2-(3,4-dihydroxyphenyl)-8-(3,4-dihydroxyphenyl)-3,4-dihydro-2H,14H-8,14-methanochromeno[7,8-d][1,3]benzodioxocine-3,5-diol and (2R,3S,8R,14R)-2-(3,4-dihydroxyphenyl)-8-(3,4-dihydroxyphenyl)-3,4-dihydro-2H,14H-8,14-methanochromeno[7,8-d][1,3]benzodioxocine-3,5-diol Yield=89%

Major isomer (60%)

$^1$H NMR (400 MHz, CD$_3$CN) δ 7.50-6.75 (m, 10H), 6.09 (s, 1H), 4.64 (d, J=8.0 Hz, 1H), 4.33 (br, 1H), 4.06-3.92 (m, 1H), 2.93-2.72 (m, 1H), 2.57-2.42 (m, 1H), 2.32-2.08 (m, 2H).

Minor isomer (40%)

$^1$H NMR (400 MHz, CD$_3$CN) δ 7.50-6.75 (m, 10H), 6.10 (s, 1H), 4.73 (d, J=8.0 Hz, 1H), 4.25 (br, 1H), 4.06-3.92 (m, 1H), 2.93-2.72 (m, 1H), 2.57-2.42 (m, 1H), 2.32-2.08 (m, 2H).

Compound A-1D:

5-[(2R,3S,8S,14S)-2-(3,4-dihydroxyphenyl)-3,5-dihydroxy-3,4-dihydro-2H,14H-8,14-methanochromeno[7,8-d][1,3]benzodioxocin-8-yl]benzene-1,2,3-triol and 5-[(2R,3S,8R,14R)-2-(3,4-dihydroxyphenyl)-3,5-dihydroxy-3,4-dihydro-2H,14H-8,14-methanochromeno[7,8-d][1,3]benzodioxocin-8-yl]benzene-1,2,3-triol Yield=80%

Major isomer (60%)

¹H NMR (400 MHz, CD₃OD) δ 7.12 (dd, J=7.6, 1.6 Hz, 1H), 7.09-6.70 (m, 8H), 6.09 (s, 1H), 4.60 (d, J=8.0 Hz, 1H), 4.32 (t, J=2.8 Hz, 1H), 4.00 (m, 1H), 2.95 (dd, J=16.4, 5.6 Hz, 1H), 2.53 (dd, J=16.4, 8.0 Hz, 1H), 2.21 (dd, J=13.2, 2.8 Hz, 1H), 2.12 (dd, J=13.2, 2.8 Hz, 1H).

Minor isomer (40%)

¹H NMR (400 MHz, CD₃OD) δ 7.24 (dd, J=7.6, 1.2 Hz, 1H), 7.09-6.70 (m, 8H), 6.09 (s, 1H), 4.74 (d, J=7.2 Hz, 1H), 4.25 (t, J=2.8 Hz, 1H), 4.04 (m, 1H), 2.86 (dd, J=16.4, 5.2 Hz, 1H), 2.57 (dd, J=16.4, 8.0 Hz, 1H), 2.15 (dd, J=13.2, 2.8 Hz, 1H), 2.08 (dd, J=13.2, 2.8 Hz, 1H).

Compound A-1E:

(2R,3S,8S,14S)-2-(3,4-dihydroxyphenyl)-8-(4-hydroxyphenyl)-12-nitro-3,4-dihydro-2H,14H-8,14-methanochromeno[7,8-d][1,3]benzodioxocine-3,5-diol and (2R,3S,8R,14R)-2-(3,4-dihydroxyphenyl)-8-(4-hydroxyphenyl)-12-nitro-3,4-dihydro-2H,14H-8,14-methanochromeno[7,8-d][1,3]benzodioxocine-3,5-diol Yield=83%

Major isomer (60%)

¹H NMR (400 MHz, CD₃OD) δ 7.99 (d, J=2.8 Hz, 1H), 7.77 (dd, J=8.8, 2.8 Hz, 1H), 7.52-7.40 (m, 2H), 7.08-6.78 (m, 6H), 6.07 (s, 1H), 4.59 (d, J=8.0 Hz, 1H), 4.34 (t, J=2.8 Hz, 1H), 4.11 (ddd, J=16.4, 8.0, 5.6 Hz, 1H), 2.95 (dd, J=16.4, 5.6 Hz, 1H), 2.49 (dd, J=16.4, 8.4 Hz, 1H), 2.26-2.01 (m, 2H).

Minor isomer (40%)

¹H NMR (400 MHz, CD₃OD) δ 8.14 (d, J=2.8 Hz, 1H), 7.84 (dd, J=8.8, 2.8 Hz, 1H), 7.52-7.40 (m, 2H), 7.08-6.78 (m, 6H), 6.07 (s, 1H), 4.68 (d, J=8.0 Hz, 1H), 4.27 (t, J=2.8 Hz, 1H), 3.94 (ddd, J=16.4, 8.0, 5.6 Hz, 1H), 2.88 (dd, J=16.4, 5.6 Hz, 1H), 2.54 (dd, J=16.4, 8.4 Hz, 1H), 2.26-2.01 (m, 2H).

Major isomer (60%)

¹³C NMR (100 MHz, CD₃OD) δ 159.30, 158.88, 152.66, 151.51, 146.40, 146.20, 142.41, 133.10, 131.50, 129.98, 127.07, 124.57, 124.36, 124.24, 124.08, 121.07, 119.57, 117.34, 116.40, 115.90, 115.46, 105.56, 103.13, 100.89, 96.34, 83.04, 68.06, 33.31, 29.09, 27.85.

Minor isomer (40%)

¹³C NMR (100 MHz, CD₃OD) δ 159.38, 158.88, 156.12, 152.50, 151.48, 146.15, 145.85, 142.37, 133.06, 131.04, 129.84, 127.07, 124.57, 124.36, 124.08, 121.07, 119.57, 117.42, 116.80, 116.26, 115.90, 105.38, 102.98, 100.86, 96.36, 83.58, 68.79, 33.39, 28.79, 27.85.

Compound A-1F:

(2R,3S,8S,14S)-2,8-bis-(3,4-dihydroxyphenyl)-12-nitro-3,4-dihydro-2H,14H-8,14-methanochromeno[7,8-d][1,3]benzodioxocine-3,5-diol and (2R,3S,8R,14R)-2,8-bis-(3,4-dihydroxyphenyl)-12-nitro-3,4-dihydro-2H,14H-8,14-methanochromeno[7,8-d][1,3]benzodioxocine-3,5-diol Yield=76%

Major isomer (60%)

¹H NMR (400 MHz, CD₃OD) δ 8.01 (br, 1H), 7.94 (dd, J=8.8, 2.0 Hz, 1H), 7.18-6.78 (m, 7H), 6.09 (s, 1H), 4.61 (d, J=7.6 Hz, 1H), 4.37 (br, 1H), 4.14 (m, 1H), 2.95 (dd, J=16.4, 5.2 Hz, 1H), 2.51 (dd, J=16.4, 8.4 Hz, 1H), 2.32-2.06 (m, 2H).

Minor isomer (40%)

¹H NMR (400 MHz, CD₃OD) δ 8.16 (br, 1H), 7.91 (dd, J=8.8, 2.0 Hz, 1H), 7.18-6.78 (m, 7H), 6.09 (s, 1H), 4.70 (d, J=7.6 Hz, 1H), 4.32 (br, 1H), 3.95 (m, 1H), 2.89 (dd, J=16.4, 5.2 Hz, 1H), 2.55 (dd, J=16.4, 8.4 Hz, 1H), 2.32-2.06 (m, 2H).

Major isomer (60%)

¹³C NMR (100 MHz, CD₃OD) δ 159.38, 156.16, 152.66, 151.54, 146.82, 146.23, 145.89, 142.46, 133.76, 131.53, 130.07, 124.41, 124.29, 121.03, 118.21, 117.34, 116.79, 116.24, 115.92, 115.39, 114.06, 105.57, 103.11, 100.80, 96.30, 83.50, 68.09, 33.46, 29.05, 27.88.

Minor isomer (40%)

¹³C NMR (100 MHz, CD₃OD) δ 159.45, 156.16, 152.51, 151.54, 146.42, 146.17, 145.89, 142.41, 133.76, 131.86, 129.93, 124.61, 124.12, 119.49, 118.27, 117.41, 116.38, 116.24, 115.92, 115.39, 114.06, 105.40, 102.95, 100.80, 96.30, 83.58, 68.78, 33.55, 28.73, 27.88.

Compound A-1G:

5-[(2R,3S,8S,14S)-2-(3,4-dihydroxyphenyl)-3,5-dihydroxy-12-nitro-3,4-dihydro-2H,14H-8,14-methanochromeno[7,8-d][1,3]benzodioxocin-8-yl]benzene-1,2,3-triol and 5-[(2R,3S,8R,14R)-2-(3,4-dihydroxyphenyl)-3,5-dihydroxy-12-nitro-3,4-dihydro-2H,14H-8,14-methanochromeno[7,8-d][1,3]benzodioxocin-8-yl]benzene-1,2,3-triol Yield=81%

Major isomer (60%)

¹H NMR (300 MHz, CD₃OD) δ 8.20 (d, J=2.7 Hz, 1H), 8.02 (dd, J=9.0, 2.7 Hz, 1H), 7.13-6.70 (m, 6H), 6.10 (s, 1H), 4.65 (d, J=7.8 Hz, 1H), 4.47 (t, J=2.4 Hz, 1H), 4.16 (m, 1H), 2.94 (dd, J=16.2, 5.6 Hz, 1H), 2.48 (dd, J=16.2, 8.4 Hz, 1H), 2.43-2.23 (m, 2H).

Minor isomer (40%)

¹H NMR (300 MHz, CD₃OD) δ 8.08 (d, J=2.7 Hz, 1H), 8.05 (dd, J=9.0, 2.7 Hz, 1H), 7.13-6.70 (m, 6H), 6.12 (s, 1H), 4.78 (d, J=7.8 Hz, 1H), 4.43 (t, J=2.4 Hz, 1H), 3.96 (m, 1H), 2.85 (dd, J=16.2, 5.6 Hz, 1H), 2.54 (dd, J=16.2, 8.4 Hz, 1H), 2.43-2.23 (m, 2H).

Compound A-1H:

(2R,3S,8S,14S)-2-(3,4-dihydroxyphenyl)-8-(3,4,5-trihydroxyphenyl)-3,4-dihydro-2H,14H-8,14-methanochromeno[7,8-d][1,3]benzodioxocine-3,5,12-triol and (2R,3S,8R,14R)-2-(3,4-dihydroxyphenyl)-8-(3,4,5-trihydroxyphenyl)-3,4-dihydro-2H,14H-8,14-methanochromeno[7,8-d][1,3]benzodioxocine-3,5,12-triol Yield=47%

Major isomer (60%)

¹H NMR (300 MHz, CD₃COCD₃) δ 8.40-6.51 (m, 8H), 6.10 (s, 1H), 4.69 (d, J=7.8 Hz, 1H), 4.27 (t, J=2.8 Hz, 1H), 4.04-3.84 (m, 1H), 3.02-2.86 (m, 1H), 2.63-2.47 (m, 1H), 2.26-2.10 (m, 2H).

Minor isomer (40%)

¹H NMR (300 MHz, CD₃COCD₃) δ 8.40-6.51 (m, 8H), 6.12 (s, 1H), 4.67 (d, J=7.8 Hz, 1H), 4.18 (t, J=2.8 Hz, 1H), 4.04-3.84 (m, 1H), 3.02-2.86 (m, 1H), 2.63-2.47 (m, 1H), 2.26-2.10 (m, 2H).

Compound A-1I:

(2R,3S,8S,14R)-2,8-bis(3,4-dihydroxyphenyl)-10-methoxy-3,4-dihydro-2H,14H-8,14-methanochromeno[7,8-d][1,3]benzodioxocine-3,5-diol and (2R,3S,8R,14S)-2,8-bis(3,4-dihydroxyphenyl)-10-methoxy-3,4-dihydro-2H,14H-8,14-methanochromeno[7,8-d][1,3]benzodioxocine-3,5-diol Yield=70%
Major isomer (65%)
$^1$H NMR (300 MHz, CD$_3$COCD$_3$) δ 7.30-6.65 (m, 9H), 6.13 (s, 1H), 4.60 (d, J=7.8 Hz, 1H), 4.35 (t, J=3.0 Hz, 1H), 4.20-3.94 (m, 1H), 3.75 (s, 3H), 3.02 (dd, J=16.5, 5.6 Hz, 1H), 2.55 (dd, J=16.5, 8.7 Hz, 1H), 2.30 (dd, J=13.2, 3.0 Hz, 1H), 2.18 (dd, J=13.2, 3.0 Hz, 1H).

Minor isomer (35%)
$^1$H NMR (300 MHz, CD$_3$COCD$_3$) δ 7.30-6.65 (m, 9H), 6.14 (s, 1H), 4.73 (d, J=8.1 Hz, 1H), 4.28 (t, J=3.0 Hz, 1H), 4.20-3.94 (m, 1H), 3.77 (s, 3H), 2.95 (dd, J=16.5, 5.6 Hz, 1H), 2.59 (dd, J=16.5, 8.7 Hz, 1H), 2.25 (dd, J=13.2, 3.0 Hz, 1H), 2.15 (dd, J=13.2, 3.0 Hz, 1H).

Compound A-1J:

(2R,3S,8R,14R)-2-(3,4-dihydroxyphenyl)-8-(3,4-dimethoxyphenyl)-3,4-dihydro-2H,14H-8,14-methanochromeno[7,8-d][1,3]benzodioxocine-3,5-diol and (2R,3S,8S,14S)-2-(3,4-dihydroxyphenyl)-8-(3,4-dimethoxyphenyl)-3,4-dihydro-2H,14H-8,14-methanochromeno[7,8-d][1,3]benzodioxocine-3,5-diol Yield=83%
Major isomer (55%)
$^1$H NMR (400 MHz, CD$_3$COCD$_3$) δ 7.38-6.74 (m, 10H), 6.16 (s, 1H), 4.62 (d, J=8.0 Hz, 1H), 4.38 (t, J=3.0 Hz, 1H), 4.13 (m, 1H), 3.85 (m, 3H), 3.83 (m, 3H), 3.03 (dd, J=16.4, 5.6 Hz, 1H), 2.57 (dd, J=16.4, 8.0 Hz, 1H), 2.34 (dd, J=13.6, 3.0 Hz, 1H), 2.25 (dd, J=13.6, 3.0 Hz, 1H).

Minor isomer (45%)
$^1$H NMR (400 MHz, CD$_3$COCD$_3$) δ 7.38-6.74 (m, 10H), 6.18 (s, 1H), 4.73 (d, J=8.0 Hz, 1H), 4.30 (t, J=3.0 Hz, 1H), 4.01 (m, 1H), 3.84 (m, 3H), 3.83 (m, 3H), 2.97 (dd, J=16.4, 5.2 Hz, 1H), 2.61 (dd, J=16.4, 8.0 Hz, 1H), 2.28 (dd, J=13.6, 3.0 Hz, 1H), 2.22 (dd, J=13.6, 3.0 Hz, 1H).

Major isomer (55%)
$^{13}$C NMR (100 MHz, CD$_3$COCD$_3$) δ 156.20, 154.25, 153.39, 152.68, 150.91, 146.75, 146.64, 146.48, 133.09, 132.82, 129.18, 128.99, 122.56, 121.17, 119.97, 116.88, 116.32, 116.13, 113.07, 107.63, 103.59, 100.36, 97.13, 83.72, 69.29, 57.17, 57.10, 34.90, 29.95, 28.51.

Minor isomer (45%)
$^{13}$C NMR (100 MHz, CD$_3$COCD$_3$) δ 156.17, 154.31, 153.22, 152.70, 151.46, 146.78, 146.70, 140.54, 133.01, 129.71, 129.54, 129.03, 121.29, 117.55, 116.72, 116.67, 116.41, 111.79, 107.46, 103.35, 100.34, 97.13, 96.40, 84.38, 69.11, 57.17, 57.10, 34.98, 29.66, 28.51.

Compound A-1K:

(2R,3S,8R,14R)-2-(3,4-dihydroxyphenyl)-11-methoxy-8-(3,4,5-trimethoxyphenyl)-3,4-dihydro-2H,14H-8,14-methanochromeno[7,8-d][1,3]benzodioxocine-3,5-diol and (2R,3S,8S,14S)-2-(3,4-dihydroxyphenyl)-11-methoxy-8-(3,4,5-trimethoxyphenyl)-3,4-dihydro-2H,14H-8,14-methanochromeno[7,8-d][1,3]benzodioxocine-3,5-diol Yield=33%
Major isomer (60%)
$^1$H NMR (400 MHz, CD$_3$COCD$_3$) δ 7.20-6.73 (m, 8H), 6.14 (s, 1H), 4.61 (d, J=8.0 Hz, 1H), 4.34 (t, J=3.2 Hz, 1H), 3.97 (m, 1H), 3.88 (m, 6H), 3.76 (m, 3H), 3.71 (m, 3H), 2.91 (dd, J=16.4, 5.6 Hz, 1H), 2.53 (dd, J=16.4, 8.4 Hz, 1H), 2.34 (dd, J=13.6, 3.2 Hz, 1H), 2.25 (dd, J=13.6, 3.2 Hz, 1H).

Minor isomer (40%)
$^1$H NMR (400 MHz, CD$_3$COCD$_3$) δ 7.20-6.73 (m, 8H), 6.15 (s, 1H), 4.70 (d, J=8.0 Hz, 1H), 4.24 (t, J=3.2 Hz, 1H), 4.09 (m, 1H), 3.87 (m, 6H), 3.76 (m, 3H), 3.74 (m, 3H), 3.01 (dd, J=16.4, 5.6 Hz, 1H), 2.57 (dd, J=16.4, 8.4 Hz, 1H), 2.29 (dd, J=13.6, 3.2 Hz, 1H), 2.23 (dd, J=13.6, 3.2 Hz, 1H).

Compound A-1L:

5-[(2R,3R,8S,14S)-2-(3,4-dihydroxyphenyl)-3,5-dihydroxy-12-nitro-3,4-dihydro-2H,14H-8,14-methanochromeno[7,8-d][1,3]benzodioxocin-8-yl]benzene-1,2,3-triol and 5-[(2R,3R,8R,14R)-2-(3,4-dihydroxyphenyl)-3,5-dihydroxy-12-nitro-3,4-dihydro-2H,14H-8,14-methanochromeno[7,8-d][1,3]benzodioxocin-8-yl]benzene-1,2,3-triol Yield=81%
Major isomer (60%)
$^1$H NMR (300 MHz, CD$_3$OD) δ 8.26 (d, J=2.7 Hz, 1H), 8.03-6.94 (m, 7H), 6.55 (s, 1H), 4.70-4.48 (m, 2H), 4.08 (m, 1H), 2.94 (dd, J=16.2, 5.6 Hz, 1H), 2.53 (dd, J=16.2, 9.6 Hz, 1H), 2.38-2.19 (m, 2H).

Minor isomer (40%)
$^1$H NMR (300 MHz, CD$_3$OD) δ 8.05 (d, J=2.7 Hz, 1H), 8.03-6.94 (m, 7H), 6.56 (s, 1H), 4.70-4.48 (m, 2H), 3.88 (m, 1H), 2.99 (dd, J=16.2, 5.6 Hz, 1H), 2.60 (dd, J=16.2, 9.6 Hz, 1H), 2.38-2.19 (m, 2H).

Compound A-1M:

(2R,3R,8S,14S)-2,8-bis-(3,4-dihydroxyphenyl)-5-hydroxy-12-nitro-3,4-dihydro-2H,14H-8,14-methanochromeno[7,8-d][1,3]benzodioxocin-3-yl 3,4,5-trihydroxybenzoate and (2R,3R,8R,14R)-2,8-bis-(3,4-dihydroxyphenyl)-5-hydroxy-12-nitro-3,4-dihydro-2H,14H-8,14-methanochromeno[7,8-d][1,3]benzodioxocin-3-yl 3,4,5-trihydroxybenzoate Yield=86%
Major isomer (70%)
$^1$H NMR (400 MHz, CD$_3$COCD$_3$) δ 8.18 (d, J=2.8 Hz, 1H), 8.02 (dd, J=9.2, 2.8 Hz, 1H), 7.27-6.70 (m, 8H), 6.18 (s, 1H), 5.59 (m, 1H), 5.20 (s, 1H), 4.75 (t, J=3.0 Hz, 1H), 3.11 (dd, J=17.2, 4.4 Hz, 1H), 3.01 (dd, J=17.2, 2.4 Hz, 1H), 2.54 (dd, J=13.6, 3.2 Hz, 1H), 2.45 (dd, J=13.6, 3.0 Hz, 1H).

Minor isomer (30%)

¹H NMR (400 MHz, CD₃COCD₃) δ 8.54 (d, J=2.8 Hz, 1H), 8.09 (dd, J=9.2, 2.8 Hz, 1H), 7.27-6.70 (m, 8H), 6.21 (s, 1H), 5.59 (m, 1H), 5.27 (s, 1H), 4.65 (t, J=3.0 Hz, 1H), 3.20-2.80 (m, 2H), 2.44 (m, 2H).

Compound A-1N:

(2R,3R,8S,14S)-2-(3,4-dihydroxyphenyl)-5-hydroxy-12-nitro-8-(3,4,5-trihydroxyphenyl)-3,4-dihydro-2H,14H-8,14-methanochromeno[7,8-d][1,3]benzodioxocin-3-yl 3,4,5-trihydroxybenzoate and (2R,3R,8R,14R)-2-(3,4-dihydroxyphenyl)-5-hydroxy-12-nitro-8-(3,4,5-trihydroxyphenyl)-3,4-dihydro-2H,14H-8,14-methanochromeno[7,8-d][1,3]benzodioxocin-3-yl 3,4,5-trihydroxybenzoate Yield=71%

Major isomer (60%)

¹H NMR (400 MHz, CD₃OD) δ 8.42 (d, J=2.8 Hz, 1H), 8.07 (dd, J=8.8, 2.8 Hz, 1H), 7.12-6.48 (m, 7H), 6.12 (s, 1H), 5.53 (m, 1H), 5.18 (s, 1H), 4.57 (t, J=3.0 Hz, 1H), 3.16-2.71 (m, 2H), 2.49-2.26 (m, 2H).

Minor isomer (40%)

¹H NMR (400 MHz, CD₃OD) δ 8.17 (d, J=2.8 Hz, 1H), 8.00 (dd, J=8.8, 2.8 Hz, 1H), 7.12-6.48 (m, 7H), 6.11 (s, 1H), 5.57 (m, 1H), 5.10 (s, 1H), 4.67 (t, J=3.0 Hz, 1H), 3.16-2.71 (m, 2H), 2.49-2.26 (m, 2H).

Compound A-2A:

(2R,3S,8S,14S,15S)-2,8-bis-(3,4-dihydroxyphenyl)-15-methyl-12-nitro-3,4-dihydro-2H,14H-8,14-methanochromeno[7,8-d][1,3]benzodioxocine-3,5-diol and (2R,3S,8R,14R,15R)-2,8-bis-(3,4-dihydroxyphenyl)-15-methyl-12-nitro-3,4-dihydro-2H,14H-8,14-methanochromeno[7,8-d][1,3]benzodioxocine-3,5-diol Yield=75%

Major isomer (55%)

¹H NMR (400 MHz, CD₃OD) δ 8.00 (d, J=2.8 Hz, 1H), 7.97 (dd, J=8.8, 2.8 Hz, 1H), 7.06-6.79 (m, 7H), 6.14 (s, 1H), 4.62 (d, J=8.0 Hz, 1H), 4.15 (m, 1H), 4.14 (m, 1H), 2.97 (dd, J=16.4, 5.6 Hz, 1H), 2.53 (dd, J=16.4, 8.4 Hz, 1H), 2.35 (dd, J=7.2, 2.4 Hz, 1H), 0.78 (d, J=6.8 Hz, 3H).

Minor isomer (45%)

¹H NMR (400 MHz, CD₃OD) δ 8.15 (d, J=2.8 Hz, 1H), 7.90 (dd, J=8.8, 2.8 Hz, 1H), 7.06-6.79 (m, 7H), 6.15 (s, 1H), 4.70 (d, J=8.0 Hz, 1H), 4.13 (m, 1H), 3.95 (ddd, J=13.6, 8.0, 5.6 Hz, 1H), 2.90 (dd, J=16.4, 5.6 Hz, 1H), 2.56 (dd, J=16.4, 8.4 Hz, 1H), 2.32 (dd, J=7.2, 2.4 Hz, 1H), 0.74 (d, J=6.8 Hz, 3H).

Compound A-2B:

(2R,3S,8S,14S,15S)-2,8-bis-(3,4-dihydroxyphenyl)-15-ethyl-12-nitro-3,4-dihydro-2H,14H-8,14-methanochromeno[7,8-d][1,3]benzodioxocine-3,5-diol and (2R,3S,8R,14R,15R)-2,8-bis-(3,4-dihydroxyphenyl)-15-ethyl-12-nitro-3,4-dihydro-2H,14H-8,14-methanochromeno[7,8-d][1,3]benzodioxocine-3,5-diol Yield=79%

Major isomer (55%)

¹H NMR (400 MHz, CD₃OD) δ 8.20 (d, J=2.8 Hz, 1H), 7.90 (dd, J=8.8, 2.8 Hz, 1H), 7.11-6.80 (m, 7H), 6.16 (s, 1H), 4.72 (d, J=8.0 Hz, 1H), 4.34 (d, J=2.0 Hz, 1H), 3.98 (ddd, J=13.6, 8.0, 5.6 Hz, 1H), 2.92 (dd, J=16.4, 5.6 Hz, 1H), 2.58 (dd, J=16.4, 8.4 Hz, 1H), 2.11 (m, 1H), 1.04 (m, 2H), 0.70 (t, J=7.0 Hz, 3H).

Minor isomer (45%)

¹H NMR (400 MHz, CD₃OD) δ 8.04 (d, J=2.8 Hz, 1H), 7.86 (dd, J=8.8, 2.8 Hz, 1H), 7.11-6.80 (m, 7H), 6.15 (s, 1H), 4.68 (d, J=8.0 Hz, 1H), 4.39 (d, J=2.4 Hz, 1H), 4.14 (ddd, J=13.6, 8.0, 5.6 Hz, 1H), 2.96 (dd, J=16.4, 5.6 Hz, 1H), 2.54 (dd, J=16.4, 8.4 Hz, 1H), 2.11 (m, 1H), 1.13 (m, 2H), 0.77 (t, J=7.0 Hz, 3H).

Compound A-2C:

Methyl [(2R,3S,8S,14S,15S)-2,8-bis-(3,4-dihydroxyphenyl)-12-nitro-3,4-dihydro-2H,14H-8,14-methanochromeno[7,8-d][1,3]benzodioxocine-15-yl]acetate and Methyl [(2R,3S,8R,14R,15R)-2,8-bis-(3,4-dihydroxyphenyl)-12-nitro-3,4-dihydro-2H,14H-8,14-methanochromeno[7,8-d][1,3]benzodioxocine-15-yl] acetate Yield=83%

Major isomer (70%)

¹H NMR (400 MHz, CD₃OD) δ 8.07 (d, J=2.8 Hz, 1H), 7.95 (dd, J=8.8, 2.8 Hz, 1H), 7.10-6.70 (m, 7H), 6.17 (s, 1H), 4.71 (d, J=7.2 Hz, 1H), 4.36 (d, J=2.0 Hz, 1H), 4.15 (ddd, J=13.2, 7.2, 5.6 Hz, 1H), 3.51 (s, 3H), 2.86 (m, 1H), 2.79 (m, 1H), 2.53 (dd, J=16.4, 8.0 Hz, 1H), 2.19 (m, 1H).

Minor isomer (30%)

¹H NMR (400 MHz, CD₃OD) δ 8.18 (d, J=2.8 Hz, 1H), 7.99 (dd, J=8.8, 2.8 Hz, 1H), 7.10-6.70 (m, 7H), 6.19 (s, 1H), 4.74 (d, J=7.2 Hz, 1H), 4.32 (d, J=2.4 Hz, 1H), 3.98 (m, 1H), 3.45 (s, 3H), 2.89 (m, 1H), 2.79 (m, 1H), 2.57 (dd, J=16.4, 8.0 Hz, 1H), 2.19 (m, 1H).

Compound D-1A:

(±)-6-(3,4-dihydroxyphenyl)-12H-6,12-methanodibenzo[d,g][1,3]dioxocine-1,3-diol

Yield=76%

¹H NMR (400 MHz, CD₃COCD₃) δ 7.42 (dd, J=7.2, 1.2 Hz, 1H), 7.31 (m, 2H), 7.10 (ddd, J=10, 8.4, 2.0 Hz, 1H), 7.01 (d, 8.4 Hz, 1H), 6.92 (d, J=8.4 Hz, 1H), 6.87 (ddd, J=8.4, 7.2, 0.8 Hz, 1H), 6.05 (d, J=2.4 Hz, 1H), 6.02 (d, J=2.4 Hz, 1H), 4.42 (t, J=2.8 Hz, 1H), 2.31 (t, J=2.8 Hz, 2H).

Compound D-1B:

(±)-6-(3,4-dihydroxyphenyl)-10-nitro-12H-6,12-methanodibenzo[d,g][1,3]dioxocine-1,3-diol Yield=80%

¹H NMR (400 MHz, CD₃COCD₃) δ 8.30 (d, J=2.8 Hz, 1H), 8.02 (dd, J=8.8, 2.8 Hz, 1H), 7.25 (d, J=2.8 Hz, 1H), 7.10 (m, 2H), 6.92 (d, J=8.8 Hz, 1H), 6.10 (d, J=2.8 Hz, 1H), 6.05 (d, J=2.8 Hz, 1H), 4.53 (t, J=2.8 Hz, 1H), 2.39 (t, J=2.8 Hz, 2H).

¹³C NMR (100 MHz, CD₃COCD₃) δ 159.94, 159.23, 156.55, 154.62, 147.36, 146.44, 143.06, 134.47, 130.75, 125.12, 124.91, 119.13, 118.35, 116.66, 114.88, 106.28, 101.39, 96.84, 96.29, 34.15, 28.44.

Compound D-1C:

(±)-5-(1,3-dihydroxy-10-nitro-12H-6,12-methanod-ibenzo[d,g][1,3]dioxocin-6-yl)benzene-1,2,3-triol Yield=82%
$^1$H NMR (400 MHz, $CD_3COCD_3$) δ 8.30 (d, J=2.8 Hz, 1H), 8.02 (dd, J=8.8, 2.8 Hz, 1H), 7.10 (d, J=8.8 Hz, 1H), 6.79 (s, 2H), 6.08 (d, J=2.0 Hz, 1H), 6.04 (d, J=2.0 Hz, 1H), 4.54 (t, J=2.8 Hz, 1H), 2.37 (t, J=2.8 Hz, 2H).

Compound D-1D:

(±)-5-(1-hydroxy-10-nitro-12H-6,12-methanod-ibenzo[d,g][1,3]dioxocin-6-yl)benzene-1,2,3-triol Yield=71%
$^1$H NMR (400 MHz, $CD_3COCD_3$) δ 8.33 (d, J=2.8 Hz, 1H), 8.05 (dd, J=9.2, 2.8 Hz, 1H), 7.34 (d, J=8.8 Hz, 1H), 7.12 (d, J=9.2 Hz, 1H), 6.80 (s, 2H), 6.47 (ddd, J=7.2, 4.4, 2.4 Hz, 2H), 4.38 (t, J=2.8 Hz, 1H), 2.44 (dd, J=2.8, 1.8 Hz, 2H).

Compound D-1E:

(±)-5-(1,3-dihydroxy-12H-6,12-methanodibenzo[d,g][1,3]dioxocin-6-yl)benzene-1,2,3-triol Yield=73%
$^1$H NMR (300 MHz, $CD_3OD$) δ 7.36 (dd, J=7.5, 1.5 Hz, 1H), 7.06 (ddd, J=8.7, 6.9, 1.5 Hz, 1H), 6.85 (m, 2H), 6.74 (s, 2H), 5.83 (s, 2H), 4.33 (t, J=2.8 Hz, 1H), 2.17 (t, J=2.8 Hz, 2H).

The invention has been described with reference to various specific and preferred embodiments and techniques. However, it should be understood that many variations and modifications may be made while remaining within the spirit and scope of the invention.

All patents, patent applications, and literature cited in the specification are hereby incorporated by reference in their entirety. In the case of any inconsistencies, the present disclosure, including any definitions therein will prevail.

What is claimed is:

1. A compound of Formula A:

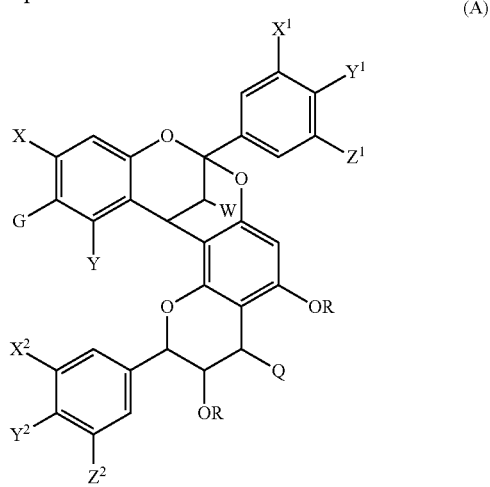

wherein $X, Y, X^1, Y^1, Z^1$ and $X^2, Y^2$, and $Z^2$ are each individually H, OH, $N(R)_2$, $(C_1-C_6)$alkoxy, or $(C_2-C_6)$alkanoyloxy;

G is OH, $(C_1-C_6)$alkoxy, $(C_2-C_6)$alkanoyloxy, $N(R)_2$, or $NO_2$;

W is H, OH, $(C_1-C_6)$alkyl, $(C_1-C_6)$alkoxy, $(C_1-C_6)$hydroxyalkyl or $(C_1-C_6)$alkoxylcarbonyl$(C_1-C_6)$alkyl;

Q is H or a single bond to $C_8$ of formula (C):

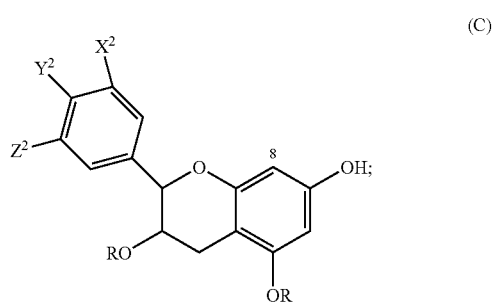

and each R is individually H, $(C_1-C_4)$alkyl, $(C_2-C_6)$alkanoyl, or $(C_6-C_{14})$arylC(O), wherein aryl is optionally substituted with 1, 2, or 3 X.

2. The compound of claim 1 wherein G is H, $NO_2$, or $(C_1-C_4)$alkoxy.

3. The compound of claim 1 wherein X and Y are H, OH, or $(C_1-C_4)$alkoxy.

4. The compound of claim 1 wherein $X^1, Y^1$, and $Z^1$ are H, OH, or $(C_1-C_4)$alkoxy.

5. The compound of claim 1 wherein $X^1$ is H, and $Y^1$ and $Z^2$ are OH or $OCH_3$.

6. The compound of claim 1 wherein each of $X^2, Y^2$, and $Z^2$ is OH.

7. The compound of claim 1 wherein W is H, OH, $(C_1-C_4)$alkyl, $(C_1-C_4)$alkoxy, or $(C_1-C_4)$alkoxycarbonyl$(C_1-C_2)$alkyl.

8. The compound of claim 1 wherein Q is H.

9. The compound of claim 1 wherein each R is individually H or substituted phenylC(O).

* * * * *

UNITED STATES PATENT AND TRADEMARK OFFICE
CERTIFICATE OF CORRECTION

PATENT NO.        : 8,138,358 B2
APPLICATION NO.   : 12/563909
DATED             : March 20, 2012
INVENTOR(S)       : George A. Kraus et al.

It is certified that error appears in the above-identified patent and that said Letters Patent is hereby corrected as shown below:

In column 5, line 24, delete "Apropyl@" and insert -- "propyl" --, therefor.

In column 5, line 25, delete "Aisopropyl@" and insert -- "isopropyl" --, therefor.

In column 6, line 41, delete "tartarate," and insert -- tartrate, --, therefor.

In column 13, line 21, delete "$Z^1$=H)" and insert -- $Z^1$=H) --, therefor.

In column 13, line 57, delete "(1100" and insert -- (100 --, therefor.

In column 13, line 63, delete "(1100" and insert -- (100 --, therefor.

In column 22, line 9, in Claim 1, delete "alkoxylcarbonyl" and insert -- alkoxycarbonyl --, therefor.

Signed and Sealed this
Sixteenth Day of October, 2012

David J. Kappos
*Director of the United States Patent and Trademark Office*